Figure 1:
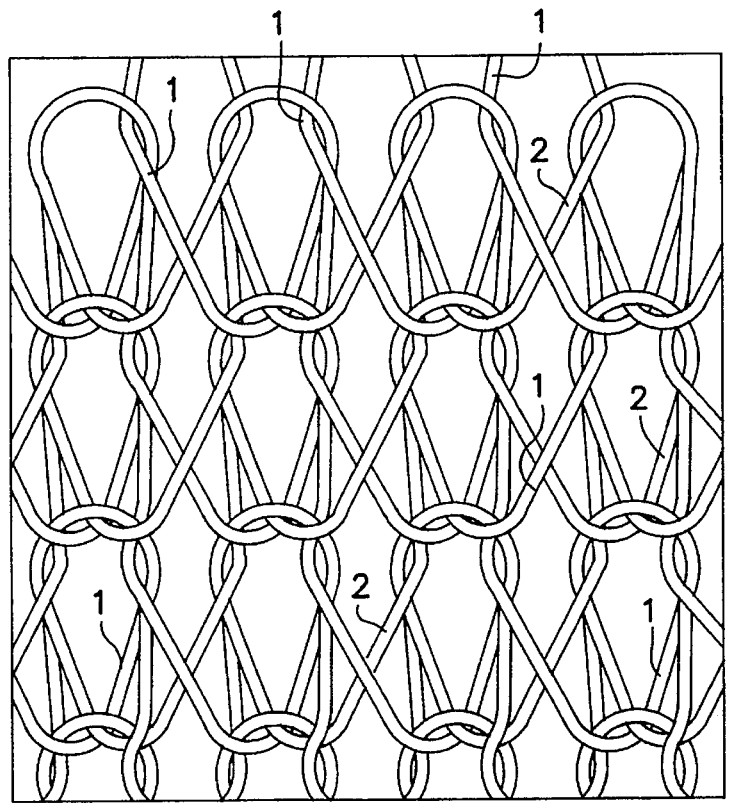

United States Patent [19]

Ceriani et al.

[11] Patent Number: 5,611,127
[45] Date of Patent: Mar. 18, 1997

[54] PROCESS FOR THE MANUFACTURE OF TEXTILE STRUCTURES SUITABLE FOR USE IN TEXTILE PROSTHESES

[75] Inventors: Leonardo Ceriani, Busto Arsizio; Gioachino Bona, Torino, both of Italy

[73] Assignee: Sorin Biomedica Cardio S.p.A., Turin, Italy

[21] Appl. No.: 589,199

[22] Filed: Jan. 22, 1996

Related U.S. Application Data

[63] Continuation of Ser. No. 101,362, Aug. 3, 1993, abandoned.

[30] Foreign Application Priority Data

Aug. 6, 1992 [IT] Italy .................. TO92A0686

[51] Int. Cl.$^6$ .................. C08G 79/02; A61F 2/06; D04B 21/00
[52] U.S. Cl. .................. 28/167; 623/1; 66/195
[58] Field of Search .................. 623/1; 66/195, 66/196, 202; 28/156, 167

[56] References Cited

U.S. PATENT DOCUMENTS

| | | | |
|---|---|---|---|
| 2,979,883 | 4/1961 | Waltz .................. | 28/156 |
| 3,853,462 | 12/1974 | Smith .................. | 623/12 |
| 3,986,828 | 10/1976 | Hoffman, Jr. et al. .................. | 8/115.5 |
| 4,047,252 | 9/1977 | Liebig et al. .................. | 623/1 |
| 4,079,602 | 3/1978 | Blore .................. | 28/156 X |
| 4,193,137 | 3/1980 | Heck .................. | 66/195 X |
| 4,209,859 | 1/1980 | Hoffman .................. | 623/1 |
| 5,158,821 | 10/1992 | Gebauer et al. .................. | 28/156 X |

FOREIGN PATENT DOCUMENTS

| | | | |
|---|---|---|---|
| 671832 | 11/1965 | Belgium .................. | 28/156 |
| 0108171 | 5/1984 | European Pat. Off. . | |
| 0306690 | 3/1989 | European Pat. Off. . | |
| 2149464 | 4/1972 | Germany . | |
| 031166 | 3/1977 | Japan .................. | 28/156 |
| 077266 | 6/1977 | Japan .................. | 28/156 |
| 3235545 | 9/1988 | Japan .................. | 28/156 |
| 9203107 | 3/1992 | WIPO . | |

OTHER PUBLICATIONS

Chemiefasern/Textilindustre, Sep. 1987, vol. 37, No. 89, pp. 794–805 (Abstract).

*Primary Examiner*—John J. Calvert
*Attorney, Agent, or Firm*—George P. Hoare, Jr.; Rogers & Wells

[57] ABSTRACT

The prosthesis is manufactured by knitting a foundation yarn with a high degree of heat-shrinkability and at least one effect yarn which is substantially heat stable, immersing the resulting fabric in boiling water so as to shrink the foundation yarn and thereby reduce its permeability to liquids while not affecting the effect yarn significantly so that it is possible to obtain good velvet effects without resorting to very high overfeed rates for the effect yarn.

16 Claims, 4 Drawing Sheets

PROCESS FOR THE MANUFACTURE OF TEXTILE STRUCTURES SUITABLE FOR USE IN TEXTILE PROSTHESES

This is a continuation of application Ser. No. 08/101,362, filed Aug. 3, 1993, now abandoned.

The present invention relates in general to the manufacture of textile prostheses such as, for example, tubular prostheses (with a linear or branched development) for the replacement of vessels or patches of prosthetic material intended to be used in local repair operations.

In a solution widely known in the art, such prostheses are manufactured by a textile process such as, for example, a warp knitting process.

In particular, the act of choosing an arrangement of the warp yarn on the frame such that the final product has a general velvet-like appearance over all (velour or double velour) is known (see for example the U.S. Pat. Nos. 4,047,252 and 4,193,137).

It is equally known that a product made by a textile manufacturing process, which is very good as regards softness and the presence and nature of the velour effect, has an equivalent permeability to liquids (and therefore to blood) which is too high. In other words, if the prosthesis were to be used as obtained from the knitting process, at least in the initial phase after implant it would not ensure effective containment of the blood fluid inside the vessel.

For this reason, a process is known (see the U.S. Pat. Nos. 3,853,462, 3,986,828 and 4,209,859) involving subjecting the fabric to shrinking. This process is generally executed chemically by means of reagents which cause the yarn constituting the fabric to swell, thereby shortening and widening the yarn itself and thus reducing the spaces or gaps between adjacent yarns in the fabric. In this way it is possible significantly to reduce the fabric permeability to fluids.

Leaving aside any problems of cost, this treatment (usually carried out with solvating and swelling agents which attack the material constituting the yarn with which the fabric has been manufactured) weakens the yarn itself which leads to a corresponding reduction in the mechanical strength of the fabric constituting the prosthesis.

In addition, in the—very frequent—case of the fabric having a velvet-like appearance, with effect loops projecting from the body formed by the foundation yarn, the chemical reagents are found to act indiscriminately both on the foundation yarn and on the effect yarn. Now, while shrinkage is beneficial as far as the foundation yarn is concerned, to reduce permeability to fluids, it is not equally so as far as the effect loops are concerned which, on the contrary, would preferably retain their original lengths, seeing that the final objective is to obtain a compact fabric with a high degree of velvet effect. At least in principle, in order to avoid sacrificing the abundant velvet effect of the finished fabric, one could consider compensating for the shrinking of the effect loops by an additional overfeed of the effect yarn during knitting. However, if the machine is operated with a high degree of overfeed of the effect yarn, knitting conditions are fairly critical, especially as regards the possible appearance of faults. If such faults are a nuisance in normal fabrics, they may have disastrous consequences in fabrics for vascular prostheses.

The object of the present invention is therefore to provide a process for the manufacture of textile prostheses that, while maintaining the advantages intrinsic to the prior art, especially as regards the criteria of fabric formation and the obtaining of an end product with an abundant velvet effect, enables the production of an end product with reduced permeability to fluids without any of the disadvantages described above as typical of the prior art.

According to the present invention, this object is achieved thanks to a process having the characteristics specifically claimed in the claims which follow. The invention also relates to a textile prosthesis which can be produced by such a process.

Figure 2:
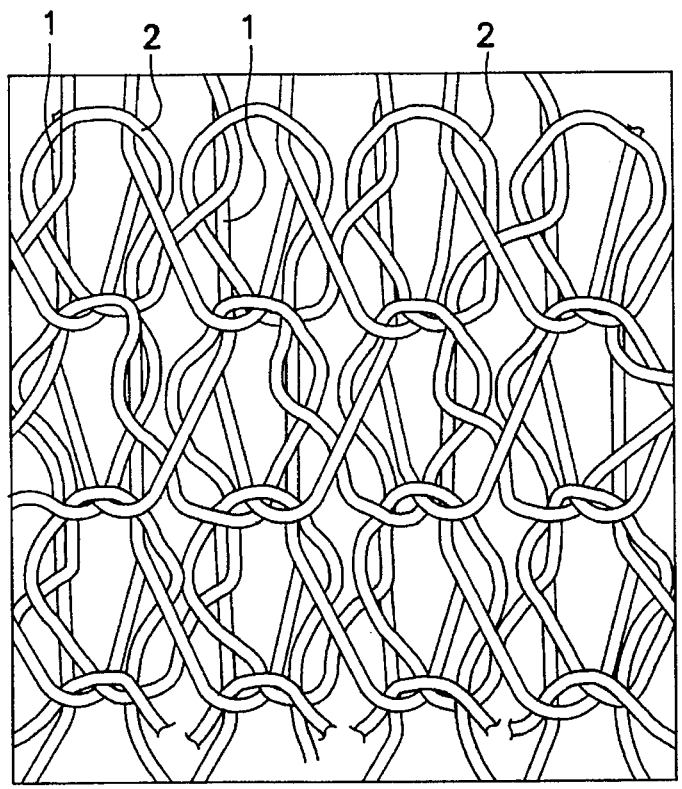

The invention will now be described, purely by way of non-limitative example, with reference to the appended drawings, in which:

FIGS. 1 and 2 show a first warp knitted structure which can be made by the process of the invention.

Figure 3:
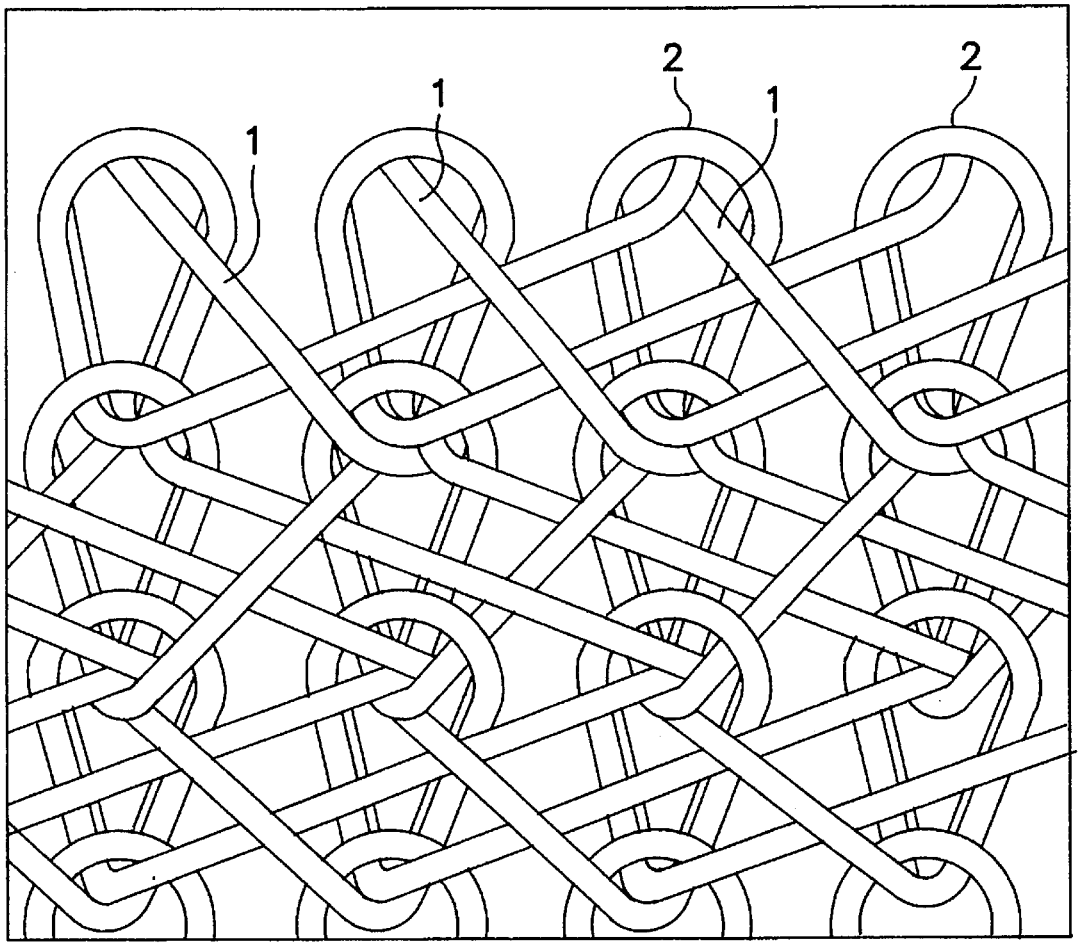
Figure 4:
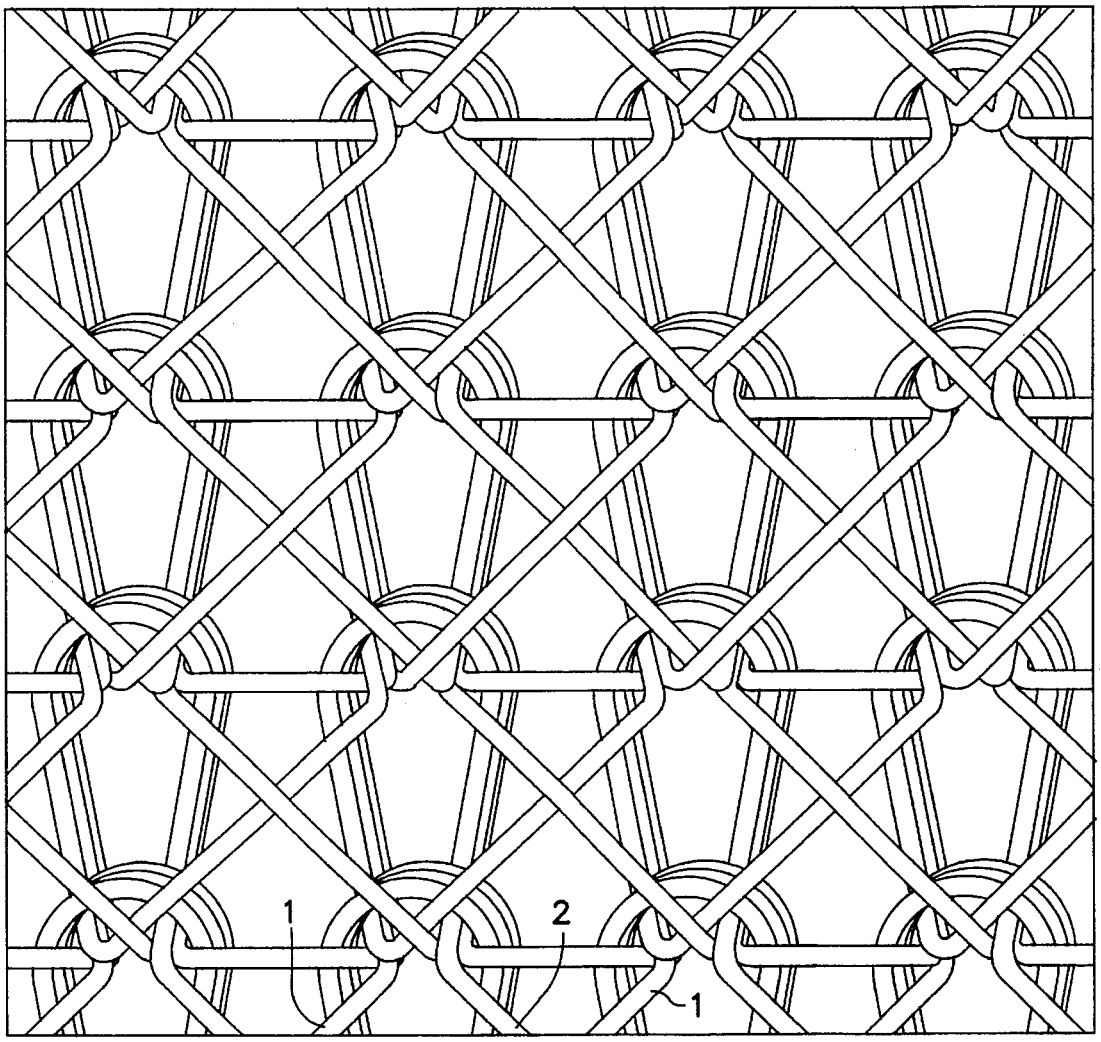
Figure 5:
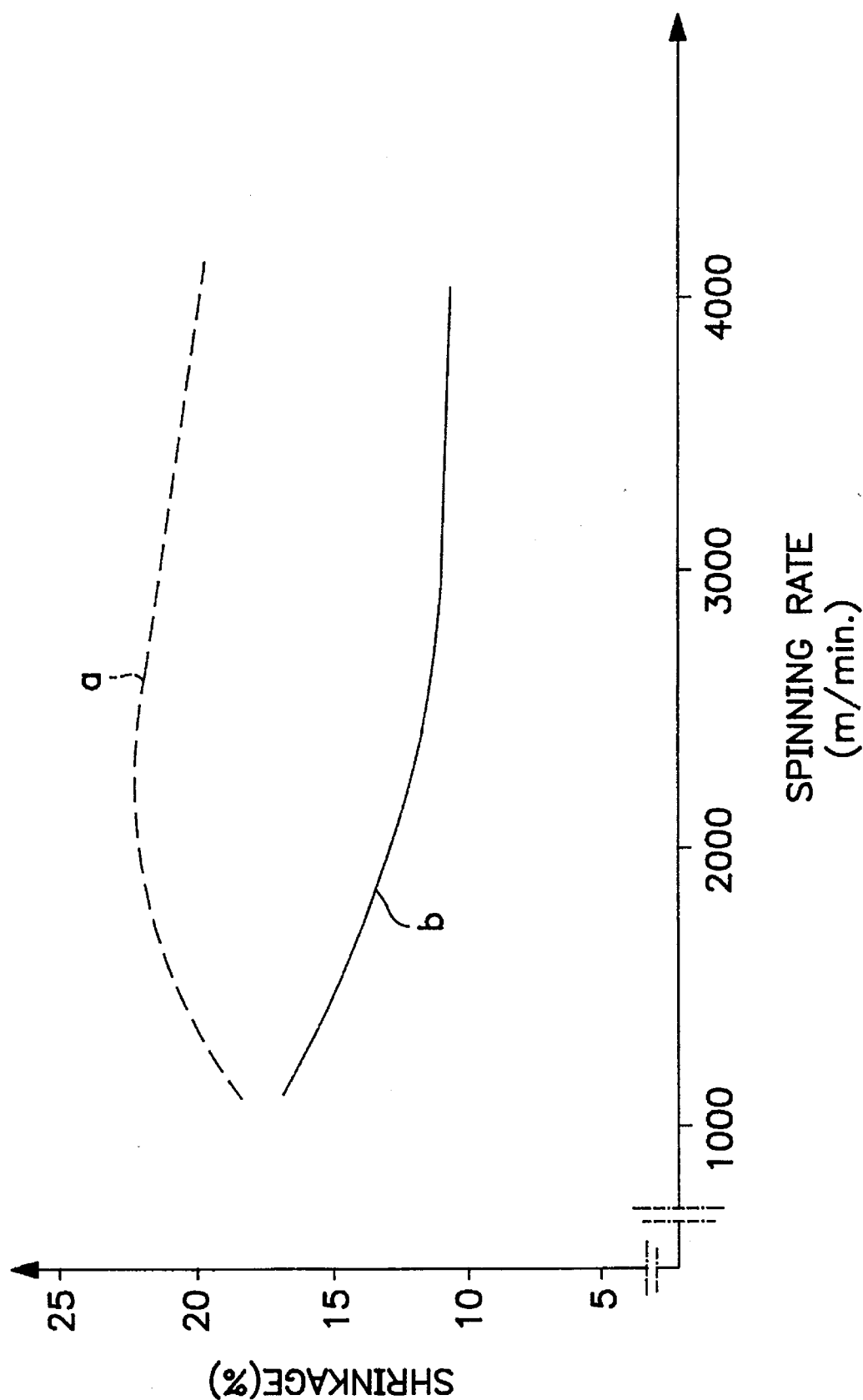

FIG. 3 shows a second warp knitted structure usable for carrying out the invention, FIG. 4 shows a further knitted structure, of an innovative type, which may also be produced by the process of the invention, and FIG. 5 is a diagram illustrating the variation in heat-shrinkability characteristics (percentage shrinkage) of a yarn which may be used in the process of the invention as a function of the conditions of manufacture of the yarn itself.

FIGS. 1 and 3 show two warp knitted structures obtained by the interlinking (in a known manner which does not require a specific description here as it is in itself not relevant to the understanding of the invention) of a so-called foundation yarn 1 (shown as light) and a so-called effect yarn 2 (shown as dark).

Naturally, since warp knitting is being considered, the yarns 1 and 2 are in fact constituted by respective families of yarns (or warps). Later in the description, and in the claims which follow, reference will be made, in general, to yarns, foundation yarns and effect yarns respectively, it being understood that these phrases in fact cover the respective warp families.

In general terms, it may be said that the foundation yarn 1 is intended to form the base or foundation structure of the fabric, while the effect yarn 2 is intended to form loops which, in the end product, project outwardly (from one or both sides of the fabric) so as to form a velvet or velour.

In the specific case, the warp knitted structure of FIG. 1 may be defined, in textile terminology, as a counterposed tricot-tricot type structure while the knitted structure of FIG. 3 may be said to have a counterposed tricot reverse locknit structure.

The warp knitted structure of FIG. 4 may be defined on the other hand as a so-called double-needle overlap tricot structure.

In this case, the foundation yarn 1 forms a far denser structure than the foundations of the fabrics of FIGS. 1 and 3: this is due to the fact that, in the fabric of FIG. 4, the foundation yarn 1 takes part in the formation of loops in two lines in each course of knitting.

A salient characteristic of the solution of the invention is the fact that, for the foundation yarn 1, a yarn, for example of polyester, is used which has a considerable shrinkage capacity, that is an "effective degree" of heat shrinkability. For example, the foundation yarn 1 used to form the structures illustrated in FIGS. 1, 3 and 4 may have a capacity to shrink at 100° C., for example in boiling water, of the order of 20–35%, with a preferred value of around 25–30% and in any case above around 10%. On the other hand, for the effect yarn 2, a substantially stabilized (heat stable) yarn is used, that is a yarn that, under the same conditions, shrinks only slightly (0.5–5%, with a preferred value of 1–1.5%).

It follows that, according to the invention, a textile prosthesis may be manufactured by first producing (by known methods) a structure such as one of those illustrated in FIGS. 1, 3 and 4 with the use of a foundation yarn 1 with a high degree of heat shrinkability paired with an effect yarn 2 with a low degree of heat shrinkability which is overfed to the extent necessary to obtain the desired velvet effect.

Subsequently, the structure thus obtained is subjected to a heat treatment (for example by immersion in boiling water) so as to shrink the foundation yarn 1 until the foundation achieves the desired degree of compactness.

Since the effect yarn 2 is of a stabilised type, the heat treatment has no appreciable effect on the effect loops, whereby the velvet effect is totally maintained and, in fact, accentuated as schematically illustrated in FIG. 2, which shows the structure of FIG. 1 after heat treatment.

This result is obtained without damaging the yarns in any way, and especially the foundation yarn 1 which thus retains all its mechanical strength.

The yarns 1 and 2 may be smooth or textured. However it appears preferable to use a smooth yarn for the highly shrinkable yarn (foundation yarn 1) but a textured stabilised yarn for the stabilised yarn (effect yarn 2).

The preferred yarn count range varies from 22 to 84 dtex with a filament/yarn count of from 1.1 to 2.0 dtex. The solution which is most preferred at present is around 44 dtex with 24–30 filaments (from 1.8 to 1.45 dtex/filament).

The low shrinkage yarn (effect yarn 2) is fed with an overfeed ratio of from 1.1 to 1.5 (the preferred solution being 1.2 to 1.35) in such a way that it forms loops either on one or on both sides of the fabric (velvet effect). If the warps are arranged on the frame in such a way that the stitches of the high-shrinkage yarn (foundation yarn 1) cover those of the other warp (effect yarn, the solution of FIGS. 1 and 2 should be particularly noted), it is possible to obtain a surface with deeper effect loops on one side of the fabric than on the other (on this point see U.S. Pat. Nos. 4,047,252 and 4,193,137). In particular, in the case of a tubular prosthesis, preference is usually given to deeper loops on the outer surface of the prosthetic vessel than on the inner surface.

Compared to the structure of FIGS. 1 and 2, the structures of FIGS. 3 and 4 have the advantage of ensuring that the foundation layer is more compact. In any case, the fact that the foundation yarn 1 is constituted by a highly heat-shrinkable yarn (in the terms set out above) offers the advantage of allowing the fabric to be subjected to heat shrinking, carried out, for example, by immersing the fabric (in particular already in the shape of a prosthesis, for example a tubular or Y-shaped prosthesis) in boiling water. Under the effect of this heat, the highly shrinkable (for example 20–35%) foundation yarn shortens, thereby rendering the foundation structure adequately compact and thus controlling its permeability. Unlike the effect of chemical shrinkage treatments, the shortening action affects only the foundation yarn 1 and not the effect loops 2 formed by a stabilised yarn. The latter do not shrink and therefore preserve in full the velvet effect created by the loops. It may be seen that, on the contrary, this effect is further enhanced as a direct result of the fact that the shrinkage involves only the foundation yarn 1 and not the effect yarns 2 (see FIG. 2).

The non-stabilised (highly shrinkable) yarn used for the foundation yarn 1 is obtained in preference by controlling the conditions in which the yarn is drawn during manufacture.

In general, in a widely known solution—see for example the article: "Vom LOY zum FOY: Herstellung und Eigenschaften glatter Filamentgarne" taken from the Chemiefasern/Textilindustrie 37./89 Jahrgang, of September 1987—synthetic yarns used in the textile industry (where it is obviously desired to reduce this shrinkage as far as possible as this characteristic is regarded in this industry as entirely negative and damaging) are obtained by a spinning and drawing process.

In particular, the yarn is exposed to a heat source, for example by advancing it along a heated plate, while under drawing conditions (for example between two motor-driven rolls).

FIG. 5 is a diagram showing the percentage shrinkage values in boiling water (on the ordinate) encountered during the drawing of a polyester yarn as a function of the spinning rate (meters/minute on the abscissa).

Both curves a and b relate to percentage shrinkage values in boiling water of polyester yarns extruded at different rates after further drawing to obtain an extensibility of 30%. Curve a, relating to a yarn drawn without any use of heat, shows how under these conditions residual percentage shrinkage values are typically found to be over 20%. Curve b, on the other hand, shows how shrinkage values obtained through conventional textile industry procedures (drawing with heat application) are always considerably lower than the value given above. In particular, the curve b shows percentage shrinkage values that are normally between 10 and 15%. In the textile industry, yarn treated in this way is usually further treated with a texturising treatment in such a way that, by regulating (in a known manner) the texturising parameters, it is possible to reduce shrinkage in boiling water to about 1%. Shrinkage values of this order may be adopted, for example, for the effect yarn 2 of FIGS. 1 to 4.

The solution of the invention thus permits the selective shrinking of a fabric forming, for example, a vascular prosthesis in such a way as to reduce its permeability to fluids (and in particular to blood fluid) thereby avoiding the traditional disadvantages of chemical processes (weakening of the fabric, reduction of mechanical strength).

In addition, the shrinking operation is more economical as it does not require the use of special chemical substances but only the immersion of the prosthesis in boiling water.

Furthermore, the solution of the invention permits selective shrinking, that is, shrinking which affects only the foundation yarn 1 and not the effect yarn 2 (velvet effect) of the prosthesis. Therefore the fact that the effect yarn does not shrink enables its rate of overfeed relative to the foundation yarn to be kept within reasonable values (for example 1.1 to 1.5) during the knitting of the fabric, thereby avoiding critical working conditions, especially as far as knitting faults are concerned.

The structure of FIG. 4 may be seen essentially as resulting from the integration of a double-needle overlap pattern foundation (yarn 1) with an effect yarn (yarn 2) knitted into the double-needle overlap foundation by methods similar to those used to knit the effect yarn 2 of the fabrics of FIGS. 1 to 3. In practice, in the structure of FIG. 4 there is a loop of effect yarn 2 (overfed so as to obtain a velvet effect) for each foundation loop, defined by two lengths of yarn 1.

As already stated, the choice of a double-needle overlap pattern for the foundation structure 1 is advantageous as it provides a foundation which is intrinsically very compact and therefore not very permeable. These properties are magnified by heat shrinkage.

What is claimed is:

1. A process for producing a dense, low porosity, mechanically tough textile prothesis comprising
   (a) knitting a first textile structure having at least two yarns wherein at least one yarn is a heat-shrinkable yarn, obtained by drawing substantially without the application of heat and knitted in a double-needle overlap tricot structure (German: Koper Trikot) for acting as a foundation yarn, and at least one other yarn is a substantially heat-stable yarn for serving as an effect yarn and being formed into projecting effect loops, wherein the heat-stable yarn is fed with an overfeed ratio to the first yarn of about 1.1 to about 1.5, and,
   (b) heat treating the resulting first textile structure by immersion in a hot liquid shrinking the heat-shrinkable yarn therein, to thereby produce a second textile structure for use in a textile prothesis.

2. The process of claim 1, wherein the heat-shrinkable yarn is a polyester yarn.

3. The process of claim 1, wherein the heat-shrinkable yarn has a degree of heat-shrinkability of greater than 10%.

4. The process of claim 3, wherein the heat-shrinkable yarn has a degree of heat-shrinkability of between 20% and 35%.

5. The process of claim 4, wherein the heat-shrinkable yarn has a degree of heat-shrinkability of between 25% and 30%.

6. The process of claim 1, wherein the heat-shrinkable yarn is a smooth yarn.

7. The process of claim 1, wherein the substantially heat-stable yarn has a degree of heat-shrinkability of between 0.5% and 5%.

8. The process of claim 1, wherein the substantially heat-stable yarn has a degree of heat-shrinkability of between 1% and 1.5%.

9. The process of claim 1, wherein the substantially heat-stable yarn is a textured yarn.

10. The process of claim 1, wherein the yarn has a yarn count of from about 22 to about 84 dtex.

11. The process of claim 1, wherein the yarn is a multifilament yarn.

12. The process of claim 11, wherein the multifilament yarn has between 24 and 30 filaments per yarn.

13. The process of claim 11, wherein the multi-filament yarn has a filament yarn count of between about 1.1 and about 2.0 dtex.

14. The process of claim 13, wherein the multi-filament yarn has a filament yarn count of between about 1.45 and about 1.8 dtex.

15. The process of claim 1, wherein the second yarn is fed with an overfeed ratio to the first yarn of between about 1.2 and about 1.35.

16. The process of claim 1, wherein the second yarn is formed into effect loops on both faces of the first textile structure.

* * * * *